US006113563A

United States Patent [19]

D'Amico et al.

[11] Patent Number: 6,113,563

[45] **Date of Patent: *Sep. 5, 2000**

[54] TRACTION DEVICE FOR PHYSICAL THERAPY

[76] Inventors: Anthony D'Amico, 362 Eckford, Troy, Mich. 48084; Joseph D'Amico, 29654 Malvina, Warren, Mich. 48093

[ * ] Notice: This patent is subject to a terminal disclaimer.

[21] Appl. No.: 08/426,938

[22] Filed: Apr. 21, 1995

[51] Int. Cl.[7] .................................. A61H 1/02; A61F 5/00

[52] U.S. Cl. .................................................. 602/32; 602/33

[58] Field of Search .................................. 602/32–36, 38, 602/40; 128/DIG. 15; 5/621–22

[56] References Cited

U.S. PATENT DOCUMENTS

| | | | |
|---|---|---|---|
| 3,003,498 | 10/1961 | Hotas . | |
| 3,114,366 | 12/1963 | Maychark | 602/33 X |
| 3,149,630 | 9/1964 | Schmidt | 602/36 |
| 3,667,457 | 6/1972 | Zumaglini . | |
| 3,871,366 | 3/1975 | Cotrel | 602/33 |
| 3,905,359 | 9/1975 | Fanstone | 602/32 |
| 4,881,728 | 11/1989 | Hunter | 5/622 |
| 5,146,641 | 9/1992 | Zwickey | 5/628 |
| 5,147,287 | 9/1992 | Jewell et al. | 602/32 |
| 5,177,823 | 1/1993 | Riach | 5/636 |

*Primary Examiner*—Richard J. Apley
*Assistant Examiner*—Denise Pothier

[57] ABSTRACT

A cervical traction device which can be used on a elevated support surface such as a bed which applies a tractive force to the back of the patient's skull approximate to the occipital bone through the use of contoured blocks which can preferably be positioned behind the patient's head and mounted on a head rest assembly. The tractive force can be continuous or cycled on and off manually during a cervical traction session. The head rest assembly slides on the bed or similar surface and can be vertically and laterally adjusted to vary the flexion-extension angle. The cervical traction device can be operated by the patient with or without the help of a second party.

22 Claims, 3 Drawing Sheets

TRACTION DEVICE FOR PHYSICAL THERAPY

FIELD OF THE INVENTION

The present invention is related to physical therapy devices. More particularly, the present invention is related to devices for administering cervical traction to the neck region of a patient. Even more particularly, the present invention is related to cervical traction devices for home-use which provide the option of administering cervical traction in either a cyclical or non-cyclical manner.

BACKGROUND OF THE INVENTION

The need for simple, low cost cervical traction devices which can be used at home to administer cervical traction to provide relief to patients with various musculo-skeletal disorders of the neck and back is well recognized. Heretofore there have been developed a great number of head halters or other devices which apply cervical traction through the head of the patient. Many of these devices engage the jaw of the patient while surrounding the head. These type of halters not only inhibit the ability of the patient to talk, they also cause aggravation of the temporomandibular (TMJ) points. As a device for administering cervical traction, these devices are less than desirable. Jaw-type head halters of this type pull from an axis offset from the spine and thereby apply an undesirable twisting moment (cervical extension) to the patient's head and neck contrary to most types of desired cervical traction. In most types of cervical traction situations, it is desirable to engage the head of the patient at the occipital area of the head rather than the chin so that the pulling axis is in straight alignment with the spine and so that the pulling force is concentrated along the posterior of the head where it is most beneficial.

Other types of devices for engaging the head to correct neck problems are cervical braces. Such braces, which are referred to as "halo type", actually contact the patient's head with pointed screws which are forced inward through the skin to make contact with the bone of the skull. Aside from the obvious pain which a patient must endure when this type of brace is employed, the potential for infection to the person's head at the points where the skin is broken is ever present.

In order to obtain effective cervical traction, heretofore, it has been necessary to go to a physical therapy department or office. At such locations cervical traction was applied using complex devices such as that described in U.S. Pat. No. 4,508,109 to Saunders which was reissued as RE 32,791. Such devices could be used to apply cervical traction. However, they were of limited value because their complexity meant that traction therapy was available to the patient only at limited locations where such devices could be permanently installed. As a result, the patient was able to obtain cervical traction less often than would have been desirable not only because of the inconvenience of having to go to such locations at only the appointed times but also because of the expense.

Therefore, it is highly desirable to provide a cervical traction device heretofore only available in a physical therapist's office which can be used by the patient at home at various intervals throughout the day so that the patient, with or without assistance, can receive the equivalent therapeutic benefits associated with more frequent cervical traction use. Unfortunately, many cervical traction devices for home use which have been developed previously are either extremely cumbersome, rely on jaw-type head halters, or fail to provide sufficient cervical traction force in a safe manner to be truly beneficial to the patient. Examples of such devices include U.S. Pat. Nos. 4,971,043 to Jones; U.S. Pat. No. 5,129,881 to Pope; U.S. Pat. No. 3,105,489 to Zivi; U.S. Pat. No. 4,674,485 to Swanson; and U.S. Pat. No. 2,954,026 to Spinks. Furthermore, none of the cervical traction devices for home use offer an effective tension cycling option.

Thus, it would be beneficial to provide a cervical traction device for use in the home which would provide cervical traction force through the skull proximate to the occiput region in a safe and easy manner which could be used by the patient in a supine position with minimal or no assistance from third parties. It is also desirable that the device provide maximum cervical traction force in a manner which is safe and beneficial to the patient-user. It is also desirable to provide a cervical traction device and method for using the same which enables the patient-user control over the course of physical therapy and its administration in concert with a program recommended by his or her physician and physical therapist.

SUMMARY OF THE INVENTION

The present invention is a device and method for providing cervical traction on a patient to address or alleviate various musculo-skeletal disorders of the cervical spine or in the upper back. The device is configured to permit the patient to administer cervical traction on him or herself with minimal or no assistance in most situations. The device of the present invention is designed to be used while the patient is lying on his or her back on a substantially horizontal surface such as a bed or other elevated support. The device of the present invention includes a head rest assembly adapted to releasably contact the patient's neck proximate to the occipital region, means for exerting tension force on the head rest assembly, and a tractive force transferring system which includes a tension line having a first end connected to the head rest assembly and a second end connected to the tension exerting means. The tractive force transferring system may also include a tension release line attached to the tension line at a point between the first and second ends thereof. The second end of the tension release line terminates in means for releasably contacting an appendage of the patient, such that the patient-user can interrupt the tension force transferred to the tension line.

The head rest assembly of the present invention can include a base which can be capable of pivoting about a first leading edge which is adapted to be in sliding contact with the elevated support surface on which the patient-user lies. A pair of members are mounted on the base proximate to the first end and protrude upward therefrom. The upwardly protruding members have a height and contour sufficient to releasably contact the skull of the patient-user.

Other objects, advantages and applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein.

DESCRIPTION OF THE PREFERRED EMBODIMENT

The cervical device 10 of the present invention provides a device and method whereby cervical traction force can be administered effectively in a variety of locations such as the home or physical therapists' office in an economical manner. The device can be used in a therapeutic program to apply cervical traction force in either a cyclical manner or in a non-cyclical manner. In the cyclical mode of operation, cervical traction force is exerted, then released, over a prescribed period of time or a number of repetitions. In the non-cyclical mode of operation, cervical traction force is applied in an essentially constant manner for a prescribed period of time. The ability to adjust the tractive force exerted is available in both the cyclical and non-cyclical operating modes.

The ability to cycle (i.e. release tension) permits the amount of cervical traction force to be increased. This is particularly advantageous as therapy progresses, because the patient-user will find it necessary to employ elevated levels of tractive force to maximize therapeutic benefit. However, if tractive force is increased, it must be cycled to prevent injury which could occur if a large tractive force is exerted for prolonged periods of time. Cycling permits a patient to employ greater tractive force with minimal risk of injury.

The cervical traction device 10 of the present invention is designed to be used with a patient in the supine position. The supine position permits relaxation of the neck muscles in order to permit optimal cervical traction effectiveness.

Figures 1, 3:
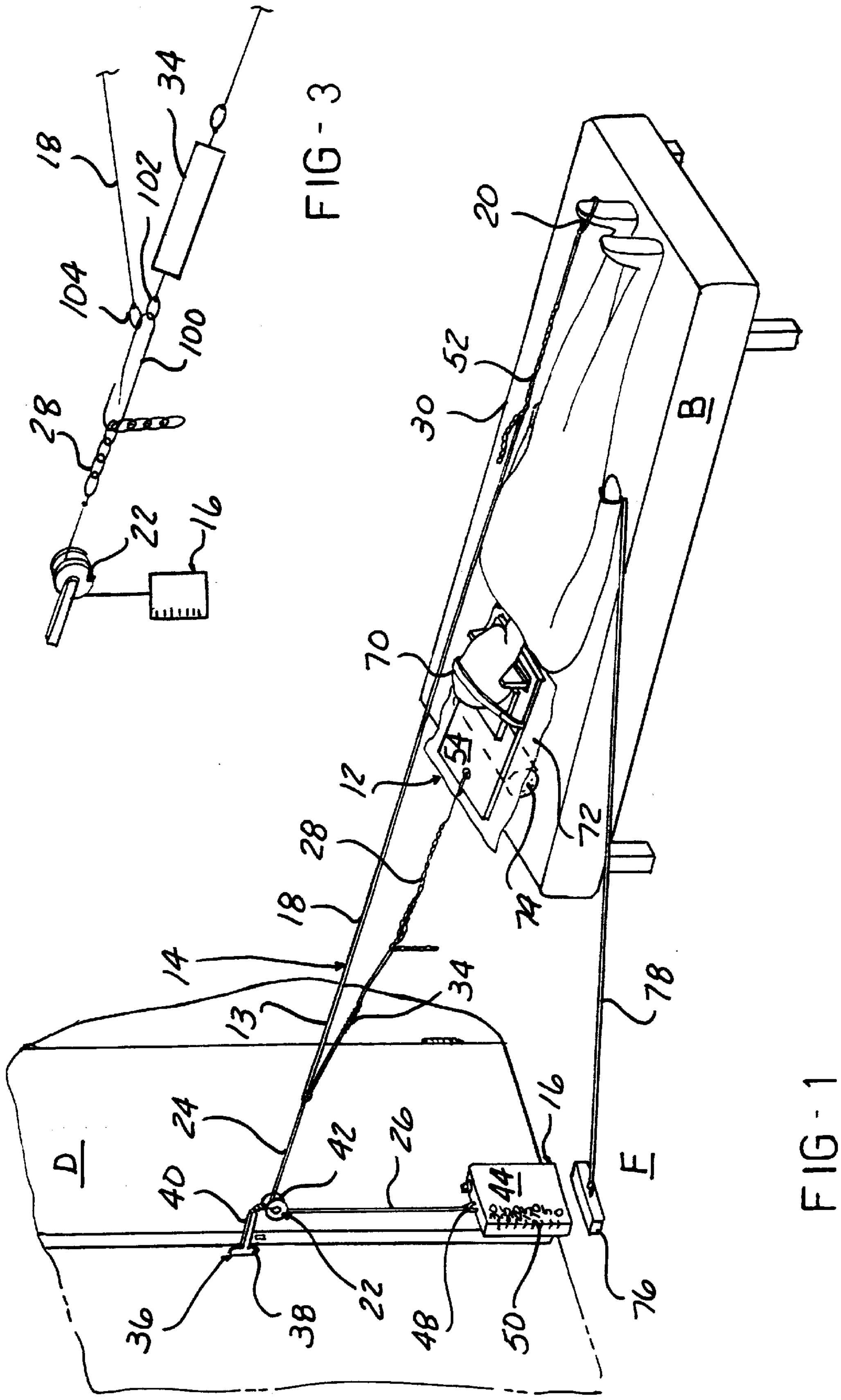
FIG. 1 is a perspective view of the cervical traction device of the present invention, configured for cyclic application.
FIG. 3 is a detail view of the linkage of the tractive force transferring system of the present invention.

The cervical traction device 10 of the present invention is composed of a head rest assembly 12 to which a suitable tension transfer system 13 including tension line 14 is suitably attached. The tension transfer system 13 is capable of transferring a tractive force from a suitable means for exerting tractive force to the head rest assembly 12. When the cyclical mode of operation is required, the tension transfer system 13 of the cervical traction device 10 of the present invention also includes means for interrupting or varying the tractive force exerted on head rest assembly 12. In the embodiment as depicted in FIG. 1, this tractive force interruption means is a tension release line 18 attached to the tension line at a first end and terminating at a second end in a means for engaging an appendage of a patient such as a loop or suitable handle device 20. In the embodiment shown in FIG. 4 the tractive force interruption means is omitted.

Figure 4:
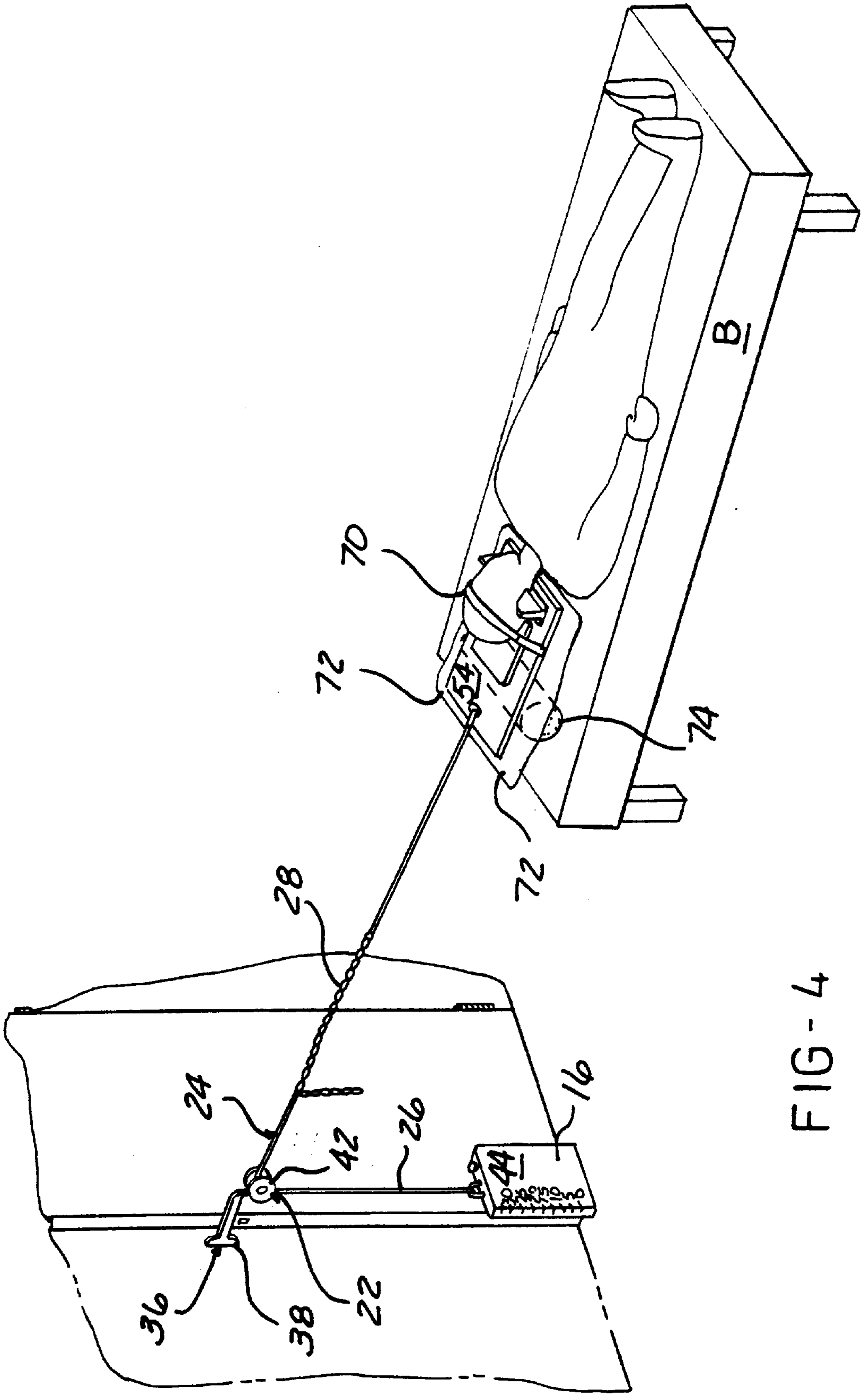
FIG. 4 is a perspective view of the cervical traction device of the present invention configured for static cervical traction.

In the embodiment as set forth in FIGS. 1 and 4, the tension line 14 has a first end attached to the head rest assembly 12 and a second end attached to the means for producing tractive force. As shown in FIGS. 1 and 4, this is preferably weight 16 which will be discussed in greater detail subsequently.

The tractive force transferring system 13 can also include a suitable pulley mechanism such as pulley device 22. In the device of the present invention, the tension line 14 extends through pulley device 22 and is moveable relative thereto. The pulley device 22 is adapted to be mounted to a suitable vertical surface at a location elevated relative to the head rest assembly 12 such as the door D depicted in FIG. 1, or to a wall, etc. The tension line 14 passes through the pulley device 22 in a manner such that the tension line 14 is provided with a first leg 24 between pulley device 22 and head rest assembly 12. The tension line 14 also includes a second leg defined by pulley device 22 and weight 16 which is essentially parallel to the vertical surface to which the pulley device 22 is attached.

In the cyclical embodiment as shown in FIG. 1, the tension release line 18 is attached at the first end thereof to the tension line 14. Preferably, the point of attachment between the tension line 14 and the tension release line 18 is located in the first leg 24 of the tension line 14, i.e. between the point at which the tension line 14 is attached to the head rest assembly 12 and the point at which the tension line 14 passes through pulley device 22. The tension release line 18 terminates in a suitable handle device 20 which can be grasped by the user to manually relieve or release the tractive force exerted by weight 16. Preferably, the patient inserts a foot in the handle device 20 to manually release the tractive force in the manner to be described subsequently.

The tension line 14 may be equipped with a suitable means for adjusting the length of the first leg 24. Such means can include any type of adjustment device. As shown in FIGS. 1 and 4, the means for adjusting the length of the first leg 24 is a linear link device 28 having a plurality of serially linked circles. The linear link device 28 is, preferably, located in the first leg 24 at a position between the point of attachment to the head rest assembly 12 and the pulley device 22. As shown in FIG. 1, the linear link device 28 is composed of a plurality of serially linked oval members to form a chain linkage. It is also to be understood that the adjustment device can be other suitable mechanisms which would permit adjustment of the lengths of first leg 24 without compromising the tractive force transferal properties of the tension line 14. Preferably, the tension line 14 is equipped with at least one clip member 30 for removable adjustment to the appropriate linked oval member of linear link device 28.

The tension line 14 may also include an optional safety shock force protector 34 located in the tension line 14 at any convenient location between head rest assembly 12 and the weight 16. The shock force protector 34 may be any suitable device which will prevent a shock force from being transferred to the cervical region of the patient. Suitable examples include, but are not limited to, shock absorbers, mechanical fuses and the like. The safety shock force protector 34 may be positioned at any location which will accomplish the necessary protection of the patient from experiencing a shock force load. As shown in FIG. 1, the safety shock force protector 34 is located between the point of attachment of the tension line 14 to head rest assembly 12 and the point of attachment of tension release line 18 to tension line 14. When employed in combination with an adjustment device such as the linear link device 28, it is preferable that the safety shock force protector 34 be positioned between the adjustment device and the point of attachment of tension release line 18. The safety shock force protector 34 can be any suitable dampening mechanism designed to eliminate or reduce any impact loading which may be transferred through tension line 14 to the head rest assembly 12.

As shown in detail in FIG. 3, the tractive force transferring system 13 of the present invention can be configured so as to have a central clip member 100 to which a suitable loop or eyelet 102 in the tension line 14 and a loop 104 in tension release line 18 may be fastened. In order to adjust the length of tension line 14 the linear linked device 28 may be positioned so as to engage the central clip member 100 in an adjustable manner as depicted in FIG. 3. One end of the linear linked device 28 is connected to a first length of suitable rope or line 15 to which a suitable weight or other tension producing means 16 is attached at the opposite end. As depicted in FIG. 3, the optional safety shock force protector 34 is also attached to the clip member 100. The optional safety shock force protector 34 is attached to an eyelet 102. A second length of suitable rope or line 17 is, in turn, attached to the head rest assembly 12. The optional tension release line 18 is also configured to be suitably attached to clip member 100 to effect attachment of the tension release line 18 to the tension line 14.

As depicted in FIG. 1, the tractive force transferring system 13 of the cervical traction device 10 of the present invention includes pulley device 22. The pulley device 22 can be mounted to any suitable surface such as door (D) either permanently or in a removable fashion. Preferably, the pulley device 22 includes a mounting support 36 to which the pulley is flexibly attached. The mounting support 36 can either be permanently attachable to a suitable vertical device such as door (D) by means of appropriate set screws or the like or can be a removable device such as shown in FIG. 1. Where the mounting support 36 is configured to be removable, the mounting support 36 includes a first planar device 38 adapted to be positioned in abutting parallel relationship to the end of door (D) and a second planar member 40 contiguously mounted to and extending perpendicularly from first planar member 38 adapted to be positioned in abutting relationship to the door surface opposed to the location of the cervical traction device 10.

In order to maintain the mounting support 36 in position on the door (D), the mounting support 36 is located above the door knob and bolt mechanism. The door (D) is closed thereby providing a secure mount which is exposed to minimal vertical or horizontal shifting. Alternately, the mounting support 36 could be mounted above a suitable door hinge.

The pulley device 22 may include a single pulley or a plurality of pulleys suitable for transferring tension to the head rest assembly 12. In the preferred embodiment, a single pulley is employed to ensure that maximum cervical traction force is transferred to the head rest assembly 12.

The pulley device 22 is mounted at a height equal to or greater than the height of the head rest assembly 12 above the floor F. In the preferred embodiment, the pulley device 22 is mounted such that the angle between the first and the second legs 24, 26 is less than 90°. It has been found that at such an angle, cervical traction force is most expeditiously transferred to the head rest assembly 12 to be imparted to the patient in the manner to be described subsequently.

In the cervical traction device 10 of the present invention, cervical traction force may be imparted by any suitable means for exerting cervical traction force such as weight 16. When a weight such as weight 16 is used, it is suspended from the terminal end of the second leg 26 of the tension line 14. As shown in FIG. 1, the weight 16 can be a suitable container device 44 having an opening 46 to permit access to the interior of the container device 44. The container device 44 also includes suitable means for attachment to the terminal end of tension line 14. As shown in FIG. 1, such attachment means can be a built-in hook 48. The container device 44 can also include a series of graduated markings 50 located on the exterior surface calibrated to correspond to weight values when the container device 44 is filled with the appropriate amount of a selected fluid material. The fluid material can be any pourable material such as sand and the like. Preferably, the fluid material employed in the container device 44 of the present invention is water. It has been found that using water as the weight medium permits easy handling and manipulation by the patient, is readily available, and can be easily disposed of as necessary. The amount of water or other fluid material to be added to the container device 44 is determined by the needs of the individual patient. The amount of cervical traction force to be imparted will vary from patient to patient depending upon the therapy protocol and rehabilitation needs of the patient. Thus, the total weight can be varied accordingly. It is also contemplated that it may be desirable to vary the amount of cervical traction force during the course of an individual's physical therapy treatment. Thus, the container device 44 of the present invention permits great flexibility in tailoring the cervical traction force to the needs of the patient.

The tractive force transfer system 13 employed in the cervical traction device 10 of the present invention may include a tension release line 18 by which the patient in cervical traction can cycle the amount of cervical traction force being applied. As indicated previously, the tension release line 18 is attached to the tension line 14 at a point between the pulley device 22 and the point of attachment to the head rest assembly 12. The tension release line 18 terminates in a suitable handle device 20 into which the user of the cervical traction device 10 can insert his or her hand or foot. Extension of the arm or leg results in the release of tractive force exerted on the head rest assembly 12. Bending of the arm or leg results in the transfer of tractive force to the head rest assembly 12. The tension release line 18 can also include a suitable means for adjusting its length such as linear linked device 30. In this manner, the cervical traction device 10 can be modified to adapt to patients of varying heights. In the preferred embodiment, the linear link device 52 has a configuration similar to that of linear link device 28.

Figure 2:
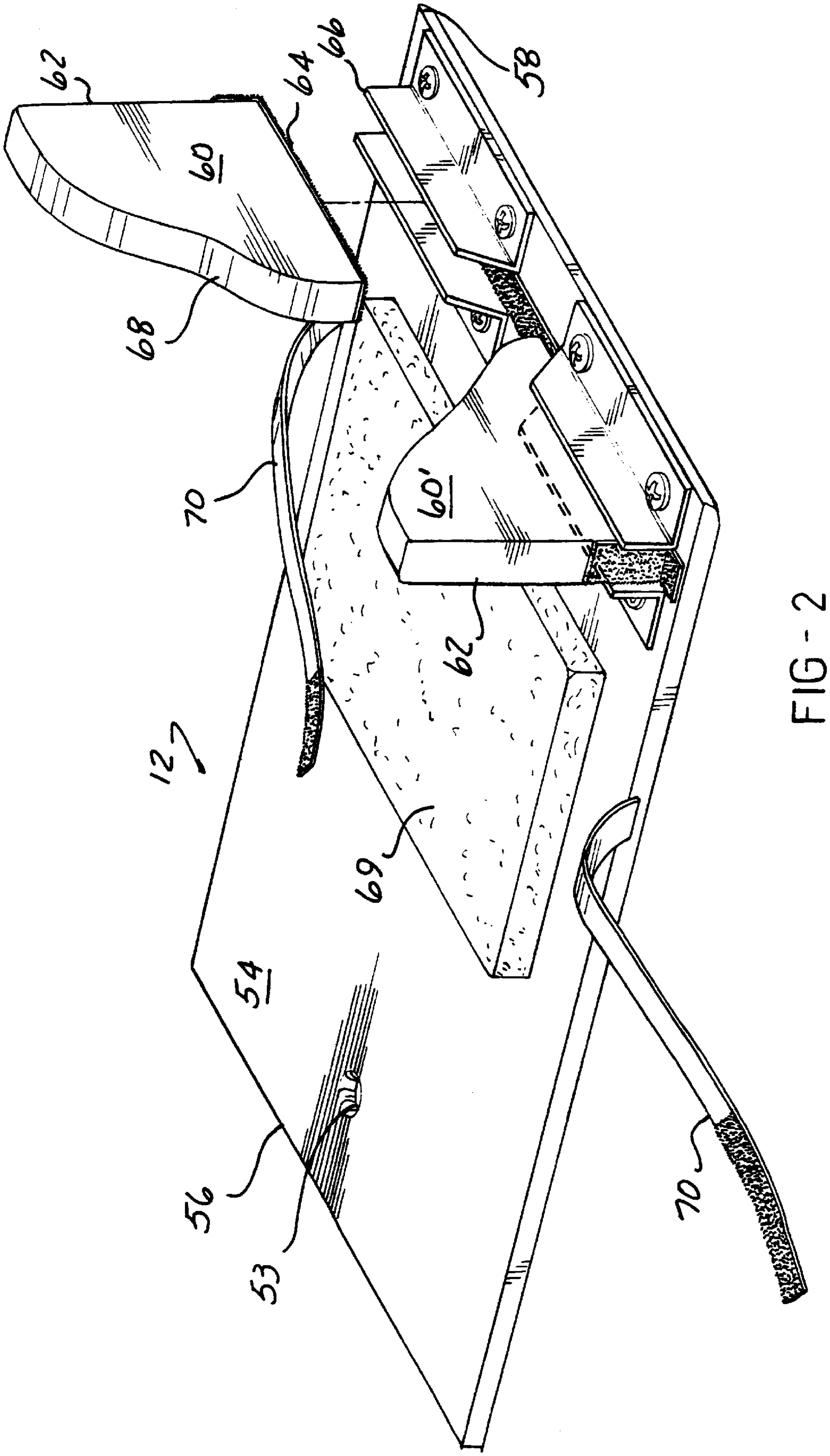
FIG. 2 is a detail perspective view of the head rest assembly of the present invention.

The head rest assembly 12 of the present invention is shown more clearly in FIG. 2. The head rest assembly 12 is composed of a base 54 having a first end 56 and an opposed second end 58. Means for attachment of the first end of the tension line 14 are located proximate to the second end 58 of the base 54 of the head rest assembly 12. As shown in FIG. 2, the attachment means is preferably an aperture 53 through which the first end of the tension line can be inserted and attached.

The first end 56 of the base 54 of the head rest assembly 12 has a forward or leading surface edge 55 which is configured and adapted to facilitate pivoting along the edge surface and provide ease of sliding during the application of tractive force. The geometric profile of the leading or forward edge 55 may be configured as a curved radius as shown in FIG. 1, a partial radius, or a suitable chamfer to facilitate sliding movement.

The base 54 of the head rest assembly 12 also includes adjustable means for releasably engaging the skull of the patient in the region proximate to the patient's neck. Preferably, engagement occurs in the occipital region located at the rear base of the skull immediately above the cervical spinal region of the neck. In the preferred embodiment, the patient engagement means are a pair of upwardly protruding members 60, 60' adjustably mounted proximate to the first end 56 of the base 54 of the head rest assembly 12 and protruding approximately perpendicularly therefrom. The upwardly protruding members 60, 60' can be mounted to the head rest assembly 12 in any manner which would facilitate the lateral adjustment of the two members relative to each other to receive the lower rear region of various patient-users' skulls. In the embodiment depicted in FIG. 1, each upwardly protruding member 60, 60' has a flat edge 62 adapted to be oriented perpendicularly to the upper surface of the base 54 of the head rest assembly 12 and a contiguous edge 64 adapted to contact the upper surface of the base 54 of the head rest assembly 12 in a laterally adjustable manner. As depicted in FIG. 2, the contiguous edge 64 is received within a suitable channel 66 which provides sufficient mechanical connection between the base 54 of the head rest assembly 12 and the given upwardly protruding member 60, 60' to prevent movement of the member 60, 60' during use of the cervical traction device 10. To further anchor the upwardly protruding members 60, 60' relative to one another, the corresponding region of the upper surface of the base 54 of the head rest assembly 12 can have a continuous strip of a suitable loop-and-eye type of fastener such as VELCRO mounted there to within channel 66. Channel 66 is preferably formed by two pairs of upwardly extending brackets 71 mounted on base 54 proximate to the forward or leading edge 55. Each bracket pair 71 has two parallel positioned members 73 with upwardly extending wall element 75 positioned a spaced distance from one another to define channel 66.

The upwardly protruding members 60, 60' may be configured to include a contoured region 68 extending between the terminal edges of the flat upwardly protruding edge 62 and the contiguous edge 64. The contoured region 68 includes an internally concave section located approximately medial between the two respective edges 62, 64 adapted to correspond to the contours of the skull of the patient-user. If desired, the contoured region 68 may have padding to increase user comfort during use. The base 54 of the head rest assembly 12 and the upwardly protruding members 60, 60' can be made of any suitable material. In the preferred embodiment, the base 54 of the head rest assembly 12 and the upwardly protruding members may be constructed from suitable plastic or wood materials.

The head rest assembly 12 of the cervical traction device 10 of the present invention can also include a skull receiving region 69 located in the upper face of the base 54 of the head rest assembly 12. Preferably, the skull receiving region 69 can be a cushioned portion mounted on the base 54 of the head rest assembly 12 to cushion any impact between the skull and the surface of the base 54 of the head rest assembly 12 during cyclical cervical traction treatment and to increase general user comfort.

The head rest assembly 12 also may optionally include forehead restraint 70 which can be employed to maintain the head of the patient-user in proper orientation during use of the cervical traction device 10 of the present invention. As shown in FIG. 2, the forehead restraint 70 is composed of two members which can be releasably joined to one another using a suitable fastening means such as a VELCRO fastener. The forehead restraint 70 is mounted to the sides of the base 54 of the head rest assembly 12 at a position between the first end 56 and the second end 58 which would permit fastening of the forehead restraint by the patient-user.

In order to transfer maximum tractive force from the tension line 14 through the head rest assembly 12 to the skull and spine of the patient-user, the cervical traction device 10 of the present invention may also include a suitable friction reduction member interposed between the lower surface of the head rest assembly 12 and the surface on which the cervical traction device 10 and the patient-user is lying, for example, bed B and the bolster shown in FIG. 1. As depicted in FIG. 1, the friction reduction device may be a separate sheet 72 positioned between the lower surface of the base 54 of the head rest assembly 12. Suitable friction-reducing materials include but are not limited to chlorofluorocarbon materials such as TEFLON materials, various other lubricous plastics, waxed paper products and the like. The friction reduction device employed in the present invention may have any suitable configuration capable of providing friction reduced movement between the elevated support surface and the head rest assembly 12. As depicted in FIG. 1, the friction reduction device may be a separate sheet 72 positioned between the lower surface of the base 54. The separate sheet 72 may be made of one or more layers which can slide on one another, with two layers being preferred. Alternately, the friction reduction device can be attached to or formed integral with the lower face of the base of the head rest assembly 12.

In order to obtain proper angular orientation between the head rest assembly 12 and the spine of the patient-user, the cervical traction device 10 of the present invention can also include a suitable bolster 74. The bolster 74 can have any suitable configuration which will permit the head rest assembly 12 to be maintained at an angular orientation between 0 and 40° from horizontal with an angle between about 0 and about 20° being preferred. The bolster 74 can have a cylindrical form such as shown in FIGS. 1 and 4. Positioning the bolster 74 proximate to or distant from the first end of the base 54 of the head rest assembly 12 will vary the angular orientation of the base of the head rest assembly 12. The bolster 74 can be any suitably configured device such as a pillow, towel, etc., which can be placed between the flat surface on which the patient-user lies during treatment and the lower face of the head rest assembly 12. Alternately, the bolster device can be integrated into the head rest assembly 12 to form a unitary member.

It can be appreciated that the configuration of the cervical traction device of the present invention permits the head rest assembly 12 to be laterally adjustable relative to an axis drawn through the neck of the patient user. This lateral adjustability can facilitate the traction procedure as well as permitting and promoting greater user comfort. In general, it is anticipated that the amount of lateral adjustment will be limited. Preferably, the head rest assembly 12 of the present invention will be adjustable to an angle between about 0° and about 20° from the axis drawn through the cervical neck region.

In using the cervical traction device 10 of the present invention, the pulley device 22 is mounted to a suitable vertical support such as door D shown in FIG. 1. The tension line 14 is inserted through the pulley device 22 and adjusted for suitable length using linear linked device 28. Similarly, the length for tension release line 18 is adjusted to the needs of the patient-user using linear linked device 30. The upwardly protruding members 60, 60' of the head rest assembly 12 are adjusted to accommodate the skull of the patient-user and a suitable amount of weight is attached to the second end of tension line 14 to provide tractive force. The amount of weight employed is generally an amount sufficient to be tolerated by the patient-user and to effectively provide an extension of the vertebrae in the neck and upper back region. It is to be understood that the amount of weight employed will vary from user to user depending on the nature of the injury and the general physical condition of the individual patient-user. It is also to be understood that the amount of weight employed for tractive force can vary during the course of treatment for a given individual due to changes in overall physical condition and in the healing experienced. The specific amount of weight is that which would be recommended by the physical therapist, physician or other health care professional.

When the cervical traction device 10 of the present invention is in position, the patient-user positions himself in the unit and begins cervical traction therapy. At the outset of each treatment session, it is desirable that there be no tractive force transferred through the tractive force transferring system 13 to the head rest assembly 12 to permit the patient-user the opportunity to obtain the proper position in the unit. This can be accomplished in one of three ways: the weight can be held by a third party until the patient-user indicates that he is ready to commence cervical traction treatment; the patient-user can maintain force on the tension release line 18 with a foot or other appendage; or the weight 16 can be mounted on a block member 76 as is shown in FIG. 1. When the block member 76 is employed with the cervical traction device 10 of the present invention, it is connected to a line 78 running to the location of the patient-user. The block 76 has a height sufficient to permit weight 16 to be freely suspended when the block is removed from contact with the weight. Once the patient-user is in position relative to the cervical traction device 10, tugging on the line 78 causes removal of the block 76 from contact with the weight 16 to initiate tractive force. A more preferred approach for entering the device of the present invention is to engage and apply force to line 18 with the proper appendage. Once this is accomplished, the patient-user has the option of pulling on line 18 to remove the force exerted on the head or to reach behind and above his head to pull the head rest assembly 12 into position with his hands. It is to be understood that this second option would minimize the need for line 78 and could be highly advantageous for certain types of injuries and conditions.

The method for administering physical therapy using the device of the present invention in the cycling mode will now be described. Once the patient-user is in position in the device 10 of the present invention, the tractive force is applied to the neck region for an interval sufficient to provide therapeutic tractive force to the affected region. The patient-user's leg or arm will be bent or flexed so that the tension release line is not carrying the tractive force. While this interval is patient-specific, it is generally understood that this interval will be an interval sufficient to provide cervical extension without injury to surrounding tissue, i.e., less than 30 minutes. At the end of this interval, the patient-user extends the leg or arm to which the tension release line is attached thereby transferring the tractive force from the head rest assembly 12 and the neck region to initiate a rest interval. The rest interval is generally a period sufficient to provide relaxation of the affected region. Without being bound to any theory, it is believed that an interval of less than one minute with an interval of about 10 seconds being preferred will be effective in many instances. At the end of the rest interval, the patient bends the leg thereby transferring tractive force back to the tension line 14, through head rest assembly 12 to the neck region. Abrupt jolts which may occur as a result of a sudden release in the tension line 14 are reduced due to the presence of safety shock force protector 34.

The cycle of cervical traction and rest is repeated for a period prescribed by the patient's physician, physical therapist or other health care giver. The interval can be defined by elapsed time or cycle repetitions as desired and tolerated by the individual patient-user. In order to time the cycles, a suitable visual or auditory timing device can be employed with the cervical traction device 10 of the present invention to assist the patient-user in maintaining the proper intervals of rest and cervical traction. Suitable devices could be but are not limited to electronic timers, mechanical timers, auditory tapes with appropriate timing signals and the like.

The cyclical repetition of alternating rest and cervical traction intervals enables the user to employ and tolerate greater traction weight than would be possible if non-cyclical cervical traction were employed. The cyclic mode of operation is usually chosen by the physician or therapist. The greater traction weight is desirable as it accomplishes greater extension of the neck region which provides enhanced therapeutic benefits.

In various instances, cyclical cervical traction may not be necessary or warranted. In such situations, the non-cyclical device as shown in FIG. 4 can be employed. When the non-cyclical device is employed, the patient-user is placed in position and tractive force is applied to the neck region for a continuous interval. As with the cyclical cervical traction device described previously, the amount of tractive force and the total cervical traction interval are patient specific and should be recommended by a physician, physical therapist, or other qualified health care professional on a case-by-case basis based on individual needs and requirements.

In either situation, use of either the cyclic or non-cyclic cervical traction device of the present invention permits the patient-user to engage in cervical traction at home or where convenient. Thus, cervical traction therapy can be performed more frequently.

The increased therapy frequency has the potential of reducing the total time the patient would require therapy and providing benefits to the patient such as an alleviation of pain in a shorter period of time. Use of the cervical traction unit of the present invention in the home provides the additional advantage in that the patient can obtain cervical traction when needed during the day rather than waiting until the next scheduled visit to the physical therapist. Prompt alleviation of pain and discomfort can prevent further patient debilitation and can actually promote healing in some instances. Additionally, the ability to employ cervical traction as needed can actually assist in the restoration of normal sleep patterns as cervical traction can be performed in bed immediately prior to sleep. The unit can be removed while the patient is in the supine position thereby preventing the affected region from experiencing a potentially painful compressive load prior to sleep.

In situations where the cyclical traction unit of the present invention is employed, and because the cervical traction device is user operated, the cycled application and release of tractive force during a therapy session is controlled by the patient. Because of this, the application and release of tractive force can be uniquely attuned to the physical indications experienced during each treatment session. Such patient control can provide subtle advantageous modifications of the general therapy regimen with each cycle in response to the physical conditions experienced. Such fine variations cannot be duplicated by a static unit or by an externally controlled device. Additionally, control of the tractive force cycle by the patient can have significant psychological benefits due to the restoration of control to the patient of at least one area of his health and well being after a period of disability. Finally, the cervical traction device of the present invention makes it possible for the patient-user to perform cyclic therapy using maximum tractive force multiple times during the course of a day or week in the comfort and privacy of his own surroundings.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A cervical traction device for use on a horizontal elevated support surface, the elevated support surface adapted to receive a patient in a supine position comprising:

a head rest assembly adapted to releasably contact the skull of a patient proximate to the occipital region, the head rest assembly comprising:

a) a base having an upper face and an opposed lower face, the upper face adapted to receive the cranial region of the skull of the patient, the base also having a first end adapted to be positioned proximate to the neck region of the patient and an opposed second end, the base also having a leading surface located proximate to the first end, the leading surface capable of facilitating slidable movement of the head rest assembly on and relative to the horizontal elevated support surface while tractive force is administered to the patient, the opposed lower face of the base adapted to directly contact and cyclically slide on the horizontal elevated support surface; and b) a pair of upwardly protruding members mounted on the base and protruding upward therefrom, the pair of upwardly protruding members positioned proximate to the first end of the base, the upwardly protruding members having a height and contour sufficient to releasably contact the skull of the patient proximate to the occipital region while the cranial region is proximate to the upper face of the base;

means for exerting tractive force on the head rest assembly; and a tractive force transferring system comprising a tension line having a first end and a second end, the first end connected to the head rest assembly, the second end attached to the tractive force exerting means.

2. The cervical traction device of claim 1 further comprising means for positioning the head rest assembly at an angle less than 50° from horizontal.

3. The cervical traction device of claim 2 wherein the head rest assembly is positioned at an angle about less than about 30° from horizontal.

4. The cervical traction device of claim 2 wherein the head rest assembly is adjustable to a lateral angle between about 0° and about 20° from an axis extending through the cervical neck region of the patient.

5. The cervical traction device of claim 2 wherein the head rest assembly positioning means comprises a bolster device, the bolster device interposed between and in direct contact with both the horizontal elevated support surface and the lower face of the base of the head rest assembly.

6. The cervical traction device of claim 2 wherein the head rest assembly further comprises:

means for adjustably positioning the upwardly protruding members relative to one another; and a deformably contourable skull receiving member positioned on the upper face of the base of the head rest assembly at a location suitable for receiving the posterior cranial region of the patient's skull.

7. The cervical traction device of claim 1 wherein the leading surface of the first end of the base defines a geometric profile configured as a curved radius.

8. The cervical traction device of claim 1 wherein the leading surface of the first end of the base defines a geometric profile which is chamfered.

9. The cervical traction device of claim 1 wherein the upwardly protruding member of the head rest assembly each comprise:

a first outer edge extending outward from the base of the head rest assembly;

a second lower edge oriented relative to the first outer edge, the second lower edge joinably contacting the base; and a third edge extending between the first outer edge and the second lower edge, the third edge oriented to receive and elevated support the portion of the patient's skull proximate to the occipital region;

wherein the upwaqrdly protruding members are positioned on the base symmetrically relative to one another.

10. The cervical traction device of claim 1 wherein the tractive force transferring system further comprises means for cyclically varying the amount of tractive force exerted on the skull by the tractive force exerting means.

11. The cervical traction device of claim 10 wherein the tractive force transferring system further comprises:

a pulley device through which the tension line extends and is moveable relative thereto such that the tension line is divided into a first leg connected to the head rest assembly and a second leg connected to the tractive force exerting means; and a tension release line having a first end and a second end, the first end of the tension release line attached directly to the first leg of the tension line, the second end of the tension release line terminating in means for releasably contacting a lower appendage of the patient.

12. The cervical traction device of claim 1 further comprising a friction reduction member having at least one elongated lubricous planar sheet interposed between and having slidable contact with the lower face of the base of the head rest assembly and the elevated support surface.

13. The cervical traction device of claim 12 wherein the friction reduction member is a polymeric member having dimensions sufficient to reduce friction between the lower face of the head rest assembly and the elevated support.

14. A cervical traction device for use on an elevated support surface providing cycling tractive force to the neck and head region of a patient-user comprising:

a head rest assembly positioned on the elevated support surface at an angle between 0° and 40° from horizontal having means for releasably contacting the skull of the patient-user proximate to the occipital region of the skull;

means for providing tractive force to the skull through the head rest assembly;

a tractive force transferring system comprising:

a) a tension line having a first end and a second end, the first end connected to the head rest assembly, the second end connected to the tractive force providing means;

b) means for cyclically varying the amount of tractive force exerted on the skull by the tractive force providing means;

c) a pulley device engageable with the tension line such that the tension line moves relative thereto, the pulley device mountable on a vertical surface external to the elevated support surface at a point elevated relative to the head rest assembly such that the tension line is divided into a first leg proximate to the head rest assembly and a second leg proximate to the tractive force providing means; and d) wherein the means for cyclically varying the amount of tractive force exerted on the skull comprises a tension release line having a first end connected directly to the tension line at a point between the Pulley device and the first end of the tension line attached to the headrest assembly and a second end terminating in means for releasably contacting a lower appendage of the patient-user.

15. The cervical traction device of claim 14 wherein the tractive force transferring means further comprises:

means for adjusting the length of the tension line;

a shock force protection device located within the tractive force transferring system; and means for adjusting the length of the tension release line wherein the tension release line is connected to the first leg of the tension line.

16. The cervical traction device of claim 15 wherein the head rest assembly further comprises:

means for laterally adjusting the position of the upwardly extending members relative to one another; and a deformable skull receiving member positioned on the upper face of the base at a location capable to receive the posterior cranial region of the skull of the patient-user.

17. The cervical traction device of claim 14 wherein the head rest assembly comprises:

a base having an upper face and an opposed lower face, the base of the head rest assembly further having a first end adapted to be positioned proximate to the neck region of the patient-user, the first end having a leading surface extending from the upper face to the lower face, the leading surface directly contactable with the elevated support surface, the base further having a second end opposed thereto, the tension line attached to the base proximate to the second end;

a pair of members mounted on the base and extending upward therefrom, the pair of members positioned proximate to the first end of the base, the members configured to releasably contact the skull of the patient-user proximate to the occipital region; and a means for permitting pivotal movement of the head rest assembly, wherein the means is pivotal between 0° and 40° on the leading surface.

18. The cervical traction device of claim 17 wherein the upwardly extending members of the head rest assembly each comprise:

a first outer edge extending outward from the base when the upwardly extending member is positioned on the base of the head rest assembly in an operative position relative thereto;

a second lower edge oriented relative to the first outer edge, the second lower edge adapted to contact the upper surface of the base; and a third edge contiguous to the first and second edges, the third edge having a contour suitable for receiving and supporting the patient-user's skull proximate to the occipital region;

wherein the upwardly extending members are positioned symmetrically on the base.

19. The cervical traction device of claim 18 further comprising a bolster in direct contact with and movably positionable between the lower surface of the base of the head rest assembly and the elevated support.

20. A cervical traction device for use on an elevated support surface providing cycling tractive force to the neck and head region of a patient-user comprising:

a head rest assembly positioned on the elevated support surface at an angle between 0° and 40° from horizontal having means for releasably contacting the skull of the patient-user proximate to the occipital region of the skull;

means for providing tractive force to the skull through the head rest assembly;

a tractive force transferring system comprising:

a) a tension line having a first end and a second end, the first end connected to the head rest assembly, the second end connected to the tractive force providing means;

b) means for cyclically varying the amount of tractive force exerted on the skull by the tractive force providing means;

c) a pulley device engageable with the tension line such that the tension line moves relative thereto, the pulley device mountable on a vertical surface external to the elevated support surface at a point elevated relative to the head rest assembly such that the tension line is divided into a first leg proximate to the head rest assembly and a second leg proximate to the tractive force providing means; and wherein the means for cyclically varying the amount of tractive force exerted on the skull comprises a tension release line having a first end connected directly to the tension line and a second end terminating in means for releasably contacting a lower appendage of the patient-user; and a friction reduction member interposed between and having slidable contact with the lower face of the base of the head rest assembly of the head rest assembly and the surface immediately adjacent thereto, wherein the friction reduction member has at least one lubricous planar sheet.

21. A method for providing patient-controlled physical therapy comprising the steps of:

positioning a patient horizontally in a physical therapy device for providing tractive force to the neck and head region, the device comprising:

a) a head rest assembly adapted to releasably contact the occipital region of a patient's skull;

b) a tension line having a first end and a second end, the first end connected to the head rest assembly;

c) means for producing tension in the tension line, the tension means connected to the second leg of the tension line; and d) a tension release line having a first and second end, the first end of the tension release line attached directly to the tension line at a point between the pulley device and the first end of the tension line attached to the headrest assembly, the second end of the tension release line terminating in means for releasably contacting an appendage of the patient;

exerting a tractive force on the neck region of the patient for an interval sufficient to provide an extension of the neck region;

releasing the tractive force exerted on the neck region of the patient, the releasing step accomplished by flexing the lower appendage of the patient to which the tension release line is attached, the tractive force being released for an interval sufficient to provide a recuperative interval for the neck region of the patient; and repeating the tension exertion and release steps for a number of times sufficient to achieve therapeutic benefits.

22. A cervical traction device for use on an elevated support surface comprising:

a head rest assembly adapted to releasably contact the skull of a patient proximate to the occipital region, the head rest assembly comprising:

a) a base having an upper face and an opposed lower face, the upper face adapted to receive the cranial region of the skull of the patient, the base also having a first end adapted to be positioned proximate to the neck region of the patient and an opposed second end, the base further comprising a channel positioned proximate to the first end of the base, the channel having a continuous strip of loop and eye attachment means positioned in the channel; and b) a pair of upwardly protruding members mounted on the base and protruding upward therefrom, the pair of upwardly protruding members positioned proximate to the first end of the base, the upwardly protruding members having a height and contour sufficient to releasably contact the skull of the patient proximate to the occipital region while the cranial region is proximate to the upper face of the base, the upwardly protruding members having a lower face receivable within the channel defined in the base, the lower face having mateable loop and eye attachment means releasably engageable with the continuous strip positioned in the channel;

means for exerting tractive force on the head rest assembly; and a tractive force transferring system comprising a tension line having a first end and a second end, the first end connected to the head rest assembly, the second end attached to the tractive force providing means.

* * * * *